United States Patent
Liang et al.

(10) Patent No.: US 11,471,481 B2
(45) Date of Patent: Oct. 18, 2022

(54) RAPID-DEPOSITION THIN-FILM FORMING COMPOSITIONS AS EFFECTIVE WOUND CARE TREATMENT

(71) Applicant: IVIEW THERAPEUTICS, INC., Wilmington, DE (US)

(72) Inventors: Bo Liang, Plainsboro, NJ (US); Xiang Jin, Nanjing (CN)

(73) Assignee: IVIEW THERAPEUTICS, INC., Wilmington, DE (US)

( * ) Notice: Subject to any disclaimer, the term of this patent is extended or adjusted under 35 U.S.C. 154(b) by 0 days.

(21) Appl. No.: 15/395,734

(22) Filed: Dec. 30, 2016

(65) Prior Publication Data
US 2018/0000858 A1  Jan. 4, 2018

Related U.S. Application Data

(60) Provisional application No. 62/355,911, filed on Jun. 29, 2016.

(51) Int. Cl.
*A61K 31/787* (2006.01)
*A61K 31/155* (2006.01)
(Continued)

(52) U.S. Cl.
CPC ............ *A61K 31/787* (2013.01); *A61F 13/00* (2013.01); *A61K 9/0014* (2013.01);
(Continued)

(58) Field of Classification Search
CPC .... A61K 31/787; A61K 47/34; A61K 31/155; A61K 31/444; A61K 9/0014;
(Continued)

(56) References Cited

U.S. PATENT DOCUMENTS

| 5,763,412 A | 6/1998 | Khan et al. |
| 7,649,045 B2 | 1/2010 | Karpowicz et al. |

(Continued)

FOREIGN PATENT DOCUMENTS

| CN | 101879283 A | * | 11/2010 |
| CN | 102406959 A | | 4/2012 |
| EP | 0761095 A2 | * | 3/1997 |

OTHER PUBLICATIONS

Office Action received in related International Application No. PCT/US2016/069420, dated Mar. 30, 2017, eight pages.

*Primary Examiner* — Hong Yu
(74) *Attorney, Agent, or Firm* — Weisun Rao; Jun Chen; Venture Partner, LLC

(57) ABSTRACT

The present invention provides thin-film forming compositions comprising an antiseptic (e.g., povidone iodine, chlorhexidine, or octenidine), a non-aqueous solvent, and a film-forming material dissolved in the non-aqueous solvent, wherein the composition yields a continuous and flexible protective film upon substantial removal of the solvent. The compositions are useful for the treatment and prevention of infections in wounds, ulcers (e.g., decubitus ulcers and stasis ulcers), cuts, or burns, or against infections from bacterial, mycobacterial, viral, fungal, or amoeba causes, as well as for prevention of such infections in appropriate clinical settings (e.g., as liquid bandages or dressings). Additionally, the compositions of this invention are also useful for the treatment of infections and as a disinfectant skin preparation for pre- and/or post-surgical operations.

15 Claims, 5 Drawing Sheets

(51) Int. Cl.
*A61K 31/444* (2006.01)
*A61K 47/34* (2017.01)
*A61K 45/06* (2006.01)
*A61K 31/125* (2006.01)
*A61F 13/00* (2006.01)
*A61K 31/045* (2006.01)
*A61K 9/70* (2006.01)
*A61K 33/18* (2006.01)
*A61K 9/00* (2006.01)

(52) U.S. Cl.
CPC .......... *A61K 9/7015* (2013.01); *A61K 31/045* (2013.01); *A61K 31/125* (2013.01); *A61K 31/155* (2013.01); *A61K 31/444* (2013.01); *A61K 33/18* (2013.01); *A61K 45/06* (2013.01); *A61K 47/34* (2013.01)

(58) Field of Classification Search
CPC .. A61K 9/7015; A61K 31/045; A61K 31/125; A61K 33/18; A61K 45/06; A61F 13/00
See application file for complete search history.

(56) References Cited

U.S. PATENT DOCUMENTS

| | | |
|---|---|---|
| 2007/0238807 A1 | 10/2007 | Safir et al. |
| 2014/0128468 A1* | 5/2014 | Bouvier ............... A61K 9/0014 514/557 |
| 2015/0150988 A1 | 6/2015 | Shalaby et al. |

* cited by examiner

0 Day

2 Days

4 Days

6 Days

8 Days

RAPID-DEPOSITION THIN-FILM FORMING COMPOSITIONS AS EFFECTIVE WOUND CARE TREATMENT

REFERENCE TO RELATED APPLICATION

The present application claims priority to U.S. Application No. 62/355,911 filed on Jun. 29, 2016, the contents of which are incorporated herein by reference in their entireties.

BACKGROUND OF THE INVENTION

Liquid bandages provide a topical skin treatment for minor cuts and sores. They are mixtures of chemicals which create a polymeric layer binding to the skin, thereby protecting the wound by keeping dirt and germs out while maintaining the moisture in the wound area. See, e.g., R. Petkewich, *Chemical & Engineering News,* 2008, vol. 86, 24, page 61. Liquid bandage is typically prepared by dissolving a polymer in a carrier solvent (usually water or an alcohol), sometimes with an added antiseptic and local anesthetic which sometimes can be the alcohol itself. These products protect the wound by forming a thin film of polymer when the carrier solvent evaporates. Examples of polymers suitable for preparing liquid bandages may include but are not limited to polyvinylpyrrolidone (water based), pyroxylin/nitrocellulose or poly(methylacrylate-isobutene-monoisopropylmaleate) (alcohol based), and acrylate or siloxane polymers (hexamethyldisiloxane or isooctane solvent based).

In addition to their use in replacing conventional bandages for minor cuts and scrapes, liquid bandages have also found use in surgical and veterinary offices, as they cause less trauma and do not have to be removed like sutures (stitches) and staples. Liquid bandages are increasingly finding use with the military, where they can be used to rapidly stanch a wound until proper medical attention can be obtained.

Existing traditional wound dressings still suffers poor waterproof, good permeability and fast curing speed. They are not conducive to the wound secretions and discharge, thus easy to allow bacterial growth and reproduction, causing or aggravating infections, especially when compared to susceptible anaerobic bacteria such as tetanus. Liquid dressings formulated with water usually take a long time to dry and, once in contact with water, would get damaged easily. It is preferable to use a solvent phase with better tolerability towards water, soap and rubbing effect to make the dressings. Therefore it's desired to develop a fast curing waterproof liquid bandage composition containing an antiseptic for wound treatment to prevent skin infection.

The most common skin preparation agents used today include products containing iodophors or chlorhexidine. However, the toxicity of higher concentrations of iodophors or chlorhexidine cannot be underestimated.

Povidone iodine (PVP-I) is a complex of polyvinylpyrrolidone (povidone or PVP) and iodine. It is also called iodophor and contains 9-12% effective iodine. It is a powerful disinfectant with a broad spectrum of applications and is strongly effective against viruses, bacteria, fungi, and mold spores. It causes little irritation on skin and has low toxicity and lasting effect, and can be used safely and easily. It basically does not cause irritation on tissue and is widely used to disinfect skin and mucous membrane, e.g., for pre-surgical cleaning and disinfection of surgical site and wound. The principle of sterilization is mainly through the release of hydrated iodine which has bactericidal effect. Povidone is hydrophilic and can carry iodine to cell membrane. When the PVP-I complex contacts the cell wall, the iodine is released and then complexes with amino acids of bacterial protein to denature it and, at the same time, oxidize the active groups of the bacteria's protoplasmic protein so that the bacteria dies rapidly. Povidone iodine is a very good bactericidal agent with no antibiotic resistance. In common use, povidone iodine's concentration is between 0.1% and 10%. Current povidone iodine preparations are in the forms of gel, suppository, cream, solution, with concentration ranging from 1% to 10%.

Chlorhexidine is an antibacterial used as an antiseptic and for other applications. It is a cationic polybiguanide (bis-biguanide). Chlorhexidine is used in disinfectants (disinfection of the skin and hands), cosmetics (additive to creams, toothpaste, deodorants, and antiperspirants), and pharmaceutical products (preservative in eye drops, active substance in wound dressings and antiseptic mouthwashes). See, e.g., Thomas Güthner et al., "Guanidine and Derivatives", *Ullman's Encyclopedia of Industrial Chemistry* (7th ed.), Wiley, 2007, p. 13. At physiologic pH, chlorhexidine salts dissociate and release the positively charged chlorhexidine cation. The bactericidal effect is a result of the binding of this cationic molecule to negatively charged bacterial cell walls. At low concentrations of chlorhexidine, this results in a bacteriostatic effect; at high concentrations, membrane disruption results in cell death. See, e.g., Jerrold B. Leikin et al., eds. "chlorhexidine Gluconate", *Poisoning and Toxicology Handbook* (4th ed.), Informa, 2008, pp. 183-484. The ChloraPrep® preoperative skin preparation currently on the market is chlorhexidine gluconate (CHG) 2% w/v and isopropyl alcohol (IPA) 70% v/v.

Since 1987, octenidine has been used in Europe as an antiseptic at a concentration of 0.1-2.0%. It is cheaper to prepare than chlorhexidine and has been a substitute for chlorhexidine, with respect to its slow action and concerns about the carcinogenic impurity 4-chloroaniline. No resistance had been observed as of 2007. See, e.g., Z. Al-Doori et al., J Antimicrob Chemother, 2007; 59: 1280-1.

Although povidone iodine commonly used at full strength as widely used and highly effective antiseptics, this concentration appears to be toxic to the cells involved in wound healing. See e.g., A. K. Balin et al., "Dilute povidone-iodine solutions inhibit human skin fibroblast growth," *Dermatol Surg., March* 2002, 28(3): 210-4. The article reported the studies of dilute PVP-I solutions on inhibition of human skin fibroblast growth and that fibroblast growth was progressively retarded at 0.01% and 0.025%, and totally inhibited by 0.1% and 1% PVP-I solutions. Partial recovery of cell growth after limited exposure of cultures to dilute solutions of PVP-I was noted. This study shows that even dilute PVP-I solutions are toxic to human fibroblasts.

This invention is based on Applicant's surprisingly unexpected discovery that rapid-deposition thin-film compositions of PVP-1, chlorhexidine, or octenidine not only exhibit sustained release properties as such to provide a long acting anti-bacterial effect, but also significantly reduce toxicity and irritation to the wound on skin. As such, the invention provides non-toxic compositions of PVP-I, chlorhexidine, or octenidine for wound healing or skin preparation.

SUMMARY OF THE INVENTION

One aspect of this invention is a rapid-deposition thin-film forming compositions each comprising an antiseptic, a non-aqueous solvent, and a film-forming material dissolved in the non-aqueous solvent, wherein the compositions yield a continuous and flexible protective film upon substantial removal of the solvent.

As used herein, the term "composition" may be interchanged with the term "formulation."

As used herein, the term "continuous and flexible protective film" refers to a film that is does not have many holes or consists of many small pieces, and the film is thin (e.g., less than 1 mm in thickness), and the film does not break when it is slightly or gently bent.

As used herein, the term substantial as in "substantial removal of the solvent" means that the majority (e.g., at least 75%, 85%, 99%, 98%, or 99%) of the solvent is removed, e.g., by evaporation.

The compositions of this invention can be in the form of a solution, cream, gel, or ointment, emulsion, or spray and are useful, e.g., for topical wound treatments (such as an instant bandage). When a composition of this invention is applied to a wound, it form a rapid deposition film on the wound when the solvent is substantially removed from the composition (e.g., by evaporation) and the film seals the wound to prevent the wound from contact germs, bacteria, or other undesired substances. In addition, the film will slowly release the antiseptic and protect the wound. The thin-film forming compositions of this invention are non-toxic to skin cells and will promote wound healing. Meanwhile, the rapid-deposition film composition is stable in storage for 1, 3, 6, 12, or even 24 months under light, without noticeable changes in physical properties or chemical composition. The rapid deposition thin-film formed on a wound not only protects the wound from infections or contamination, but also is waterproof.

In some embodiments, the antiseptic contained in the compositions of this invention includes povidone iodine (PVP-I), chlorhexidine, octenidine, or a combination thereof. Examples of chlorhexidine and octenidine suitable for the present invention include chlorhexidine digluconate and octenidine dihydrochloride, although other chlorhexidine or octenidine may be used as well.

The antiseptic can be contained in the composition at a concentration between 0.01% and 10%, between 0.1% and 2.5%, between 0.1% and 2.0%, or between 0.5% and 2.0% (weight/weight or weight/volume). Unless otherwise specified herein, the concentration of any substance in the compositions of this invention can always be either weight/weight or weight/volume.

In some specific embodiments, the rapid-deposition thin-film forming compositions of this invention contain PVP-I at a concentration between 0.01% and 5%, between 0.1% and 2.5%, or between 0.3 and 2% (weight/weight or weight/volume). Alternatively, the compositions of this invention contain chlorhexidine at a concentration between 0.1% and 2.5% (weight/weight), or octenidine at a concentration between 0.1% and 2.0% (weight/weight).

When PVP-I is the antiseptic contained in the compositions of this invention, it can be released from the film (formed upon substantial removal of the solvent of the compositions) to kill all bacterial, mycobacterial, viral, fungal, or amoeba through an extended or slow release vehicle or mechanism. This extended or slow release allows, in one aspect, to maintain a low concentration of PVP-I on the wounds or surrounding areas to eliminate toxicity, and in another aspect, to achieve longer or extended antiseptic effect against infection. The inventors unexpectedly found that the extended or slow release of PVP-I from the films formed by the compositions of this invention surprisingly had demonstrated to be non-toxic to fibroblasts.

In some embodiments, the film-forming material contained in the compositions of this invention includes polyvinylbutyral (PVB), a vinylpyrrolidone and vinyl acetate copolymer, polyvinylpyrrolidone, ethyl cellulose, nitrocellulose, poly(methylacrylate-isobutene-monoisopropylmaleate), acrylate polymer, polysiloxane, or a combination thereof. Among these materials, PVB has proved to be particularly suitable.

The film-forming material can be contained in the compositions of this invention at a concentration between 1% and 20%, between 1% and 10%, or between 5% and 10% (weight/weight or weight/volume).

In some other embodiments, the thin-film forming compositions of this invention include ethanol, propanol, isopropanol, isopentane, ethyl acetate, acetone, or a combination thereof, as the solvent or co-solvent. Among these additional compounds, ethyl acetate, acetone, or a combination thereof is particularly helpful.

The thin-film forming compositions of this invention may still include a cooling agent, a lubricant, an antimicrobial preservative, a co-solvent, a surfactant, a viscosity agent, or a bio-adhesive agent, as excipients.

Examples of suitable cooling agents contained in the compositions of this invention include, but are not limited to camphor, borneol, menthol, methone glycerin acetyl ester, methone glycerin ester, methone glycerin carboxamide, methane glycerol ketal, alkyl-substituted urea, sulfonamide, terpene analog, borneol, furanone, or phosphine oxide, and a combination thereof. Among these examples, menthol or camphor is particularly suitable. A cooling agent can provide coolness sensation on the skin and mucosal surfaces.

Lubricants can provide comfort on the wound. Examples of suitable lubricants contained in the compositions of this invention include, but are not limited to, propylene glycol, glycerin, propylene glycol, blended polyvinyl alcohol, polyvinyl alcohol, polyethylene glycol 400, light mineral oil, castor oil, hydroxypropyl methylcellulose, hypromellose, Carbopol 980, white petrolatum, soy lecithin, sodium carboxyl methylcellulose, hydroxypropyl methylcellulose, hypromellose, and a combination thereof.

Examples of suitable antimicrobial preservatives contained in the compositions of this invention include, but are not limited to, benzalkonium chloride, thimerosal, chlorobutanol, methyl paraben, propyl paraben, phenylethyl alcohol, EDTA, sorbic acid, Onamer M, and a combination thereof. The antimicrobial preservative can be contained in the compositions of this invention at a concentration between 0.001% and 1.0% (weight/weight or weight/volume). However, it is preferred that a preservative is not needed for PVP-I compositions since PVP-I is self-preservative.

Examples of co-solvent or surfactant contained in the compositions of this invention include, but are not limited to, polysorbate 20, polysorbate 60, polysorbate 80, a polyoxyethylene surfactant, a polyoxypropylene surfactant (e.g. Pluronic F-68, F-84, and P-103), cyclodextrin, tyloxapol, and a combination thereof. The co-solvent or surfactant can be contained in the composition at a level from 0.01% to 2%, from 0.01% to 1%, from 0.1% to 1%, or from 0.1% to 0.5% (weight/weight or weight/volume), although typically such co-solvents are used at a level of from 0.01% to 2% by weight.

Examples of viscosity builder agent contained in the compositions of this invention include, but are not limited to, polyvinyl alcohol, polyvinylpyrrolidone (PVP), methyl cellulose, hydroxypropylmethylcellulose, hydroxyethylcellulose, carboxymethylcellulose, hydroxypropylcellulose, or hyaluronic acid. The viscosity builder agent can be contained in the composition at a level of from 0.01% to 2%, from 0.01% to 1%, from 0.1% to 1%, or from 0.1% to 0.5% (weight/weight or weight/volume), although typically such agents are used at a level of from 0.01% to 2% by weight.

Bio-adhesive agents can be used in the compositions of this invention to increase the retention time of the drug (antiseptic) gradient over the biological substrates (skin). Examples of suitable bio-adhesive agent contained in the compositions of this invention include, but are not limited to, PVP, xanthan gum, locust bean gum, acacia gum, hydroxypropyl methylcellulose (HPMC), sodium alginate, pectin, gelatin, carbomer, polyvinylalcohol, gellan gum, tragacanth, acacia, or sodium carboxymethyl cellulose.

In still some other embodiments, the compositions of this invention include PVP-I or chlorhexidine at a concentration of 0.5% to 2.5%, PVB at a concentration of 5% to 10%, ethanol at a concentration of 50% to 60% or isopropanol at a concentration of 50% to 70%, and ethyl acetate at a concentration of 8% to 10%. These compositions may optionally further include acetone at a concentration of 20% to 25%, castor oil at a concentration of 0.1% to 1%, or camphor at a concentration of 1% to 2%.

In yet still some other embodiments, the compositions of this invention further include sugar, potassium Iodate, potassium iodide, a local anesthetic, or a topical skin adhesive.

Sugar can be optionally added to the compositions of this invention to promote wound healing as additional excipients; whereas potassium Iodate and/or potassium iodide can be added to improve stability of dilute povidone iodine solution during storage. Topical anesthetics can be added to relieve temporary pain on the wound. Examples of suitable topical anesthetics include, but are not limited to, proparacaine, lidocaine, and a combination thereof.

Topical skin adhesives have gained popularity in wound closure practices. The Skin adhesives currently on the market include derivatives of cyanoacrylates such as EpiGlu®, Histoacryl® Topical Skin Adhesive, DERMABOND ADVANCED® Topical Skin Adhesive, SurgiSeal® Adhesive. Examples of the topical skin adhesive suitable for the compositions of this invention include cyanoacrylate and a derivative thereof. The inventors have unexpectedly discovered the film-forming compositions of this invention can be combined with topical skin adhesives for the treatment and prevention of pre- and/or post-surgical infections with surprisingly good results.

As ingredients of the thin-film forming compositions of this invention, the antiseptic and topical skin adhesives (e.g., cyanoacrylates) can exist together as one mixture of the antiseptic and the skin adhesives, or they can exist as two ingredients and be placed in separate compartments in a skit/applicator or two skits/applicators. When they are placed in separate compartments, the two ingredients can be applied together at the same time or sequentially (i.e., one after the other).

The thin-film forming compositions of this invention have proven to be useful for the treatment and prevention of infections in wounds, ulcers (e.g., decubitus ulcers and stasis ulcers), cuts, or burns, or against infections from bacterial, mycobacterial, viral, fungal, or amoeba causes, as well as treatment to prevent such infections in appropriate clinical settings, e.g., as liquid bandages or dressings. Additionally, the compositions of this invention are also useful for the treatment of infections; as a disinfectant skin preparation for pre- and/or post-surgical operations.

BRIEF DESCRIPTIONS OF THE DRAWINGS

DETAILED DESCRIPTION OF THE INVENTION

Example 1: Screening of Solvent

Figure 1:
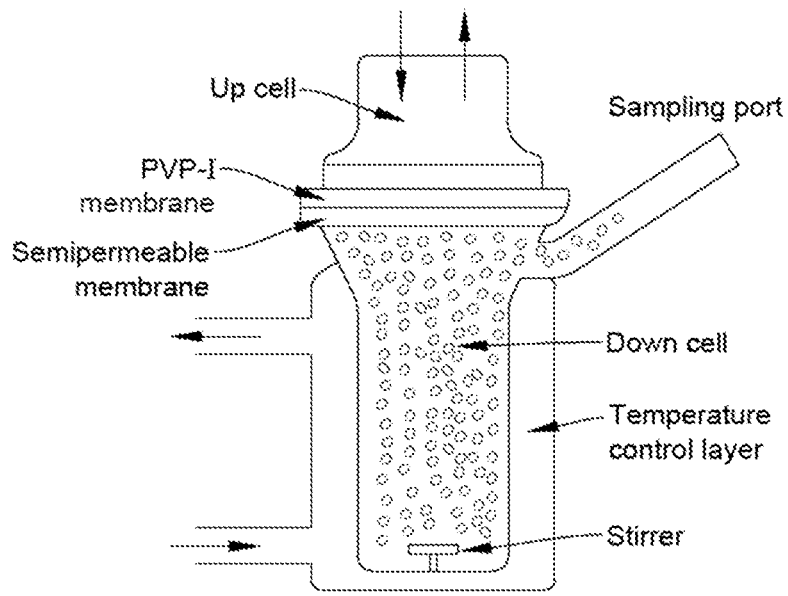
FIG. 1 shows a transdermal diffusion apparatus (Franz single-room diffusion cell) used to investigate the drug release properties of compositions of this invention.

PVP-I is a polymer complex soluble in water. To prepare a non-aqueous phase liquid dressing, the first step was to screen the solvent phase, as shown in Table 1:

TABLE 1

Solubility of Povidone Iodine (PVP-I) in Different Organic Solvents

| Sample | 1 | 2 | 3 | 4 | 5 | 6 | 7 | 8 | 9 | 10 | 11 | 12 |
|---|---|---|---|---|---|---|---|---|---|---|---|---|
| PVP-I | 0.2 g | 0.2 g | 0.2 g | 0.2 g | 0.2 g | 0.2 g | 0.2 g | 0.2 g | 0.2 g | 0.2 g | 0.2 g | 0.2 g |
| Ethanol | 4.5 g | 0 | 0 | 0 | 0 | 4.5 g | 4.5 g | 4.5 g | 4.5 g | 4.5 g | 4.5 g | 4.5 g |
| Ethyl acetate | 0 | 4.5 g | 0 | 0 | 0 | 1.5 g | 0 | 1.5 g | 1.5 g | 0 | 0 | 0 |
| Acetone | 0 | 0 | 4.5 g | 0 | 0 | 0 | 1.5 g | 1.0 g | 0 | 0 | 0 | 0 |
| Isopentane | 0 | 0 | 0 | 4.5 g | 0 | 0 | 0 | 0 | 1.0 g | 0.5 g | 1.0 g | 1.5 g |
| n-pentane | 0 | 0 | 0 | 0 | 4.5 g | 0 | 0 | 0 | 0 | 0 | 0 | 0 |
| Solubility | Very Good | | Insoluble | | | | Good | | | | Very Good | |
| Drying time | 3 Min 27 s | 0 | 0 | 0 | 0 | 3 min | 1 min 45 s | 1 min 35 s | 1 min 25 s | 2 min 37 s | 2 min 32 s | 2 min 18 s |

NOTE:
%: the percentage of total formulation volume (W/W)

To make PVP-I liquid bandage solutions to form rapid-deposition film on skin surface, low boiling-point volatile solvents were selected to study solubility of PVP-I and the time required for the solvent to evaporate to dryness. Table 1 above shows that PVP-I was readily soluble in ethanol and insoluble in ethyl acetate, acetone, isopentane and n-pentane. The use of a mixed solvent could significantly improve PVP-I's solubility. When ethanol alone was the solvent, the drying time was 3 minutes 27 seconds. A mixed solvent has even shorter drying time. Particularly, when the mixed solvent contains acetone and isopentane (which have low boiling points), drying time had been shortened to less than 2 minutes, as the mixed solvents could form azeotropes, which was easier to evaporate. Isopentane had some irritation to skin, and thus its dosage could not be too high. From the study, dosage greater than 15% of isopentane could not shorten the drying time, but instead increase the skin irritation. n-Pentane is not used because of its pungent smell. Therefore, after a preliminary study, ethanol, ethyl acetate, acetone and isopentane alone or combinations were chosen as the solvent phase in this invention.

Example 2. Pre-Formulations with Nitrocellulose as Film-Forming Material

After screening of the non-aqueous solvents, preparations of PVP-I liquid bandage pre-formulations with nitrocellulose as film-forming material were carried out as nitrocellulose has been widely used in liquid bandage products such as New Skin products. The formulation samples were left at room temperature, and their stability data were shown in Table 2:

TABLE 2

Pre-formulations with nitrocellulose as film-forming material

| | Formulation No. | | | | | | | |
|---|---|---|---|---|---|---|---|---|
| | 5 | 9 | 10 | 13 | 15 | 18 | 21 | 23 |
| Povidone iodine | 0.2 g | 0.2 g | 0.1 g | 0.2 g | 0.2 g | 0.2 g | 0.2 g | 0.1 g |
| Ethanol | 4.5 g | 4.5 g | 4.6 g | 2.5 g | 4.5 g | 6.0 g | 4.5 g | 4.5 g |
| Ethyl acetate | 0 | 0 | 0 | 4.5 g | 3.3 g | 2.2 g | 4.0 g | 3.4 g |
| Acetone | 2.5 g | 2.3 g | 2.3 g | 0 | 0 | 0 | 0 | 0 |
| Isopentane | 1.5 g | 1.5 g | 1.5 g | 1.5 g | 0.5 g | 0 | 0 | 0 |
| Nitrocellulose | 1.0 g | 1.2 g | 1.2 g | 0.8 g | 1.2 g | 0.8 g | 0.5 g | 1.0 g |
| Castor oil | 0.2 g | 0.2 g | 0.2 g | 0 | 0.2 g | 0 | 0 | 0 |
| Camphor | 0.1 g | 0 | 0 | 0 | 0.1 g | 0 | 0 | 0 |
| Mint | | 0.1 g | 0.1 g | 0 | 0 | 0 | 0 | 0 |

The results in Table 2 showed that the mixture of PVP-I and nitrocellulose was not inductive for preparing a clear liquid bandage formulation. Even after adjusting the amount of nitrocellulose, PVP-I, ethanol, or the mixture of ethyl acetate and acetone, the appearances of prepared samples were turbid and insoluble substance was observed. Layer separation was observed with all samples after they were left at the room temperature for 1 week, possibly due to the water solubility of PVP-I and hydrophobicity of nitrocellulose nitrate. After mixing, the mixture still could not be completely dissolved in the solvent, resulting in precipitations.

Example 3. Adjustment of Formulation Preparation Processes

Based on the initial screening of formulations as described in Example 2, we found that using the mixture of PVP-I and nitrocellulose to prepare a liquid bandage resulted in cloudy appearance of the prepared samples, and separation of layers was observed after samples were left at the room temperature for one week. These indicated that samples were unstable. To determine if different formulation processes could result in clear liquid bandage formulations. Shown in Table 3 below are the formulations prepared by different preparation processes:

TABLE 3

Additional Liquid Bandage Formulations

| | Formulation No. | | |
|---|---|---|---|
| | 19 | 20 | 22 |
| Povidone iodine | 0.2 g | 0.2 g | 0.2 g |
| Ethanol | 4.5 g | 4.5 g | 1.5 g |
| Ethyl acetate | 3.3 g | 3.3 g | 6.0 g |
| Nitrocellulose | 1.0 g | 1.0 g | 1.0 g |
| Initial Clarity | Turbid | Turbid | Turbid |

Preparation Process:
Formulation 19
2.5 g ethanol and 0.2 g PVP-I were mixed and stirred to dissolve until a clear violet solution was obtained with no insoluble substance observed. This clear solution was set aside. Separately, 2.0 g ethanol, 3.3 g ethyl acetate, and 1.0 g nitrocellulose were mixed and stirred to dissolve until the mixture became a transparent viscous gel with no insoluble substance observed. The PVP-I-ethanol solution and the nitrocellulose gel just prepared were mixed and stirred vigorously to give rise a cloudy mixture (i.e., a PVP-I formulation). After the PVP-I formulation was left at the room temperature for one week, layer separation was observed.
Formulation 20
A mixed solvent was prepared with 4.5 g ethanol and 3.3 g ethyl acetate. 3.9 g of the just prepared ethanol/ethyl acetate mixed solvent was then mixed with 0.2 g PVP-I and the mixture was stirred until PVP-I fully dissolved, resulting in a clear violet solution without insoluble substance. This PVP-I solution was set aside. 1.0 g nitrocellulose was added to the remaining ethanol/ethyl acetate mixed solvent and the mixture was stirred until nitrocellulose fully dissolved and the mixture transformed into a transparent viscous gel without insoluble substance remaining. The gel and the PVP-I solution were then mixed and stirred vigorously until the mixture became cloudy. After being left at the room temperature for one week, the PVP-I formulation was observed to have separated layers.
Formulation 22
A mixed solvent was prepared with 1.5 g ethanol and 6.0 g ethyl acetate. 3.75 g of the ethanol/ethyl acetate mixed solvent just prepared was mixed with 0.2 g PVP-I and the mixture was stirred until PVP-I was fully dissolve, resulting in a clear violet solution without insoluble substance. This PVP-I solution was set aside. 1.0 g nitrocellulose was added to the remaining ethanol/ethyl acetate mixed solvent and stirred until it was fully dissolved and the mixture transformed into a transparent viscous gel without insoluble substance remaining. The gel and the PVP-I solution were then mixed and stirred vigorously until the mixture became cloudy. After being left at the room temperature for one week, the PVP-I formulation was observed with layer separation.

The liquid bandage formulations with transparent appearance of this example could not be achieved through adjusting the preparation process when nitrocellulose was used as film-forming material. Precipitation formed from the mixture of PVP-I and nitrocellulose, was not a simple problem of solubility, but the compatibility of the two substances.

Example 4. Screening of Film-Forming Materials

After a film is formed the wound with the film-forming formulations of this invention, the film should be impermeable to water. As such, hydrophobic film-forming materials were selected to make film-forming formulations of this invention. After a preliminary screening of examples of the formulation of this invention and optimization of the preparation processes, samples with qualified appearance were not obtained by using nitrocellulose. The film-forming materials were selected again, and the results are shown below in Table 4:

TABLE 4

Screening of the film-forming materials

| | Formulation | | | | | | | | | |
|---|---|---|---|---|---|---|---|---|---|---|
| | 1 | 8 | 3 | 6 | 2 | 4 | 14 | 17 | 29 | 52 |
| PVP-I | 0.2 g | 0.2 g | 0.2 g | 0.2 g | 0.2 g | 0.2 g | 0.2 g | 0.2 g | 0.2 g | 0.2 g |
| Ethanol | 4.5 g | 4.5 g | 4.5 g | 4.5 g | 4.5 g | 4.5 g | 4.5 g | 4.5 g | 4.5 g | 4.5 g |
| Ethyl acetate | 2.3 g | 2.5 g | 0 | 0 | 1.9 g | 1.5 g | 3.8 g | 3.8 g | 3.3 g | 3.3 g |
| Acetone | 0 | 0 | 2.3 g | 2.5 g | 0 | 2.3 g | 0 | 0 | 0 | 0 |
| Isopentane | 1.5 g | 1.5 g | 1.5 g | 1.5 g | 1.9 g | 0 | 0 | 0 | 0.5 g | 0.5 g |
| Nitrocellulose | 1.2 g | 1.0 g | 1.2 g | 1.0 g | 1.2 g | 1.2 g | 1.2 g | 1.2 g | 0 | 0 |
| PVB | 0 | 0 | 0 | 0 | 0 | 0 | 0 | 0 | 1.2 g | 0 |
| Ethyl cellulose | 0 | 0 | 0 | 0 | 0 | 0 | 0 | 0 | 0 | 1.2 g |
| Clarity | Cloudy | Cloudy | Cloudy | Cloudy | Cloudy | Cloudy | Cloudy | Cloudy | Clear | Cloudy |

NOTE:
%: the percentage of total formulation volume (W/W)

Adjustments of the proportion of ethanol, ethyl acetate, acetone and isopentane, and change the dosage of nitrocellulose, could not improve the transparency of the product. Then, ethyl cellulose was investigated as a film-forming material, and appearance of product was cloudy, too. Polyvinylbutyral (PVB) was investigated as a film-forming material, and it unexpectedly resulted in a clear and burgundy solution. Despite different appearances of the formulations with different film-forming materials, the liquid compositions prepared with three different film-forming materials, upon application on the skin, quickly became a continuous, flexible film, and were easy to apply. Nitrocellulose, polyvinylbutyral, and ethyl cellulose were preferable film-forming materials, wherein the most preferable film-forming material was PVB.

Example 5. Screening of Mixed Solvent (I)

With ethanol, ethyl acetate, acetone and isopentane as solvents and PVB as the film-forming material, further studies of the ratio of the mixed solvent were carried out. Film formation time was measured, and formulation stability was investigated at 25° C. The results were shown below in Table 5.

As shown in Table 5, formulations using only ethanol and iso-pentane (Formulation 26 and 35), or formulations using only ethanol and ethyl acetate (Formulation 33), the film-forming time was significantly slower than the formulation using the mixture of three solvents. After being placed at 25° C. for 22 days, the viscosity of the formulations in this example, except Formulation 32, increased considerably, which resulted in each formulation forming a block with no mobility. The change of the percentage of isopentane had no effect on film-forming time. Due to its irritation to the skin and low boiling point, isopentane was ruled out as excipient of the formulations. Therefore, the preferable solvents for the formulations of this invention include the mixture of ethanol, ethyl acetate and/or acetone.

Example 6. Screening of Mixed Solvent (II)

Studies of screening of Mixed Solvent (I) showed that adding acetone into formulations could prevent increase of viscosity and agglomeration after the formulations were placed for a period of time. Further studies of the ratio of the mixed solvent were carried out. Film formation time was measured, and stability was investigated at 40° C. for 5 days and 10 days. The results are shown below in Table 6:

TABLE 5

| | Formulation | | | | | | | | | |
|---|---|---|---|---|---|---|---|---|---|---|
| | 26 | 35 | 25 | 27 | 28 | 30 | 31 | 32 | 33 | 40 |
| PVP-I | 0.2 g | 0.2 g | 0.2 g | 0.2 g | 0.2 g | 0.2 g | 0.2 g | 0.2 g | 0.2 g | 0.2 g |
| Ethanol | 8.0 g | 7.2 g | 5.0 g | 5.5 g | 4.5 g | 5.6 g | 5.6 g | 5.6 g | 5.0 g | 5.6 g |
| Ethyl acetate | 0 | 0 | 3.0 g | 2.2 g | 3.7 g | 2.2 g | 1.7 g | 0 | 3.8 g | 2.2 g |
| Acetone | 0 | 0 | 0 | 0 | 0 | 0 | 0 | 2.2 g | 0 | 0 |
| Isopentane | 0.5 g | 1.5 g | 0.5 g | 1.0 g | 0.5 g | 1.0 g | 1.5 g | 1.0 g | 0 | 1.0 g |
| PVB | 1.0 g | 0.8 g | 1.0 g | 0.8 g | 0.8 g | 0.8 g | 0.8 g | 0.8 g | 0.8 g | 0.8 g |
| Castor oil | 0.2 g | 0.2 g | 0.2 g | 0.2 g | 0.2 g | 0.1 g | 0.1 g | 0.1 g | 0.1 g | 0.1 g |
| Camphor | 0.1 g | 0.1 g | 0.1 g | 0.1 g | 0.1 g | 0.1 g | 0.1 g | 0.1 g | 0.1 g | 0.1 g |
| Film drying time after 0 day | 2 min 42 s | 2 min 35 s | 1 min 22 s | 1 min 27 s | 1 min 29 s | 1 min 30 s | 1 min 32 s | 1 min 34 s | 2 min | 1 min 25 s |
| Left at 25° C. for 22 days | | | Forming block | | | | | liquid | Forming block | |

NOTE:
%: the percentage of total formulation volume (W/W)

TABLE 6

| | Formulation | | | | | |
|---|---|---|---|---|---|---|
| | 45 | 46 | 47 | 48 | 49 | 51 |
| PVP-I | 2% | 2% | 2% | 2% | 2% | 2% |
| Ethanol | 56% | 56% | 58% | 58% | 56% | 68% |
| Ethyl acetate | 10% | 10% | 10% | 22% | 5% | 22% |
| Acetone | 22% | 22% | 22% | 0 | 27% | 0 |
| Isopentane | 0 | 0 | 0 | 10% | 0 | 0 |
| PVB | 8% | 8% | 6% | 6% | 8% | 6% |
| Castor oil | 0.5% | 0 | 0.5% | 1% | 2% | 0.5% |
| Camphor | 1.5% | 2% | 1.5% | 1% | 1.5% | 1.5% |
| Film formation time (after 5 days) | 2 min 3 s | 1 min 50 s | 1 min 10 s | — | 2 min 10 s | 1 min 40 s |
| Appearance (after 5 days) | No thread, easy to apply | No thread, easy to apply | No thread, very easy to apply | Agglomeration | No thread, easy to apply | No thread, easy to apply |
| Film formation time (after 10 days) | 1 min 44 s | 1 min 20 s | 1 min 15 s | — | 1 min 46 s | — |
| Appearance (after 10 days) | No thread, easy to apply | No thread, easy to apply | No thread, very easy to apply | — | No thread, easy to apply | Thread, viscous |

NOTE:
%: the percentage of total formulation volume (W/W)

As shown in Table 6, lowering the amount of polyvinylbutyral could not solve the problem of agglomeration after the sample was placed for a period of time. Secondly, adding acetone could greatly alleviate the problem of increasing viscosity. The film-forming time of Formulation 47 was shortest, however the film was thinner. Moreover, reducing the amount of castor oil could shorten the film-forming time. Therefore, the preferable percentages of various ingredients are: PVB around 6%-8%; solvent being the mixture of ethanol and ethyl acetate and acetone (which contained 50-60% of ethanol, about 10% ethyl acetate, about 20-30% acetone); castor oil around 0.5%, and camphor around 1%-2%.

Example 7. Screening of Polyvinylbutyral

Polyvinylbutyral (PVB) polymers with different molecular weights (MWs) were evaluated. Formulations of this invention prepared with PVBs of different MWs were placed in the dark or under light at 60° C. for 10 days. Film drying time, appearance, viscosity and available iodine content were measured as criteria to determine stability of the sample formulations. Mechanical properties of the formulations were measured as well. The results are shown below in Table 7:

TABLE 7

| | Formulation | | |
|---|---|---|---|
| | 53 | 54 | 58 |
| PVP-I | 2% | 2% | 2% |
| Ethanol | 56% | 58% | 66% |
| Ethyl acetate | 10% | 10% | 22% |
| Acetone | 22% | 22% | 0 |
| PVB (170,000-250,000) | 8% | 6% | 0 |
| PVB (90,000-120,000) | 0 | 0 | 8% |
| Castor oil | 0.5% | 0.5% | 0.5% |
| Camphor | 1.5% | 1.5% | 1.5% |
| Viscosity | 420 cps | 360 cps | 135 cps |
| Samples packed in transparent glass bottles | | | |
| Film drying time (60° C. after 10 days) | 1 min 30 s | 1 min 35 s | 1 min 10 s |
| Appearance (60° C. after 10 days) | Burgundy, supernatant liquid, no thread, easy to apply | Burgundy, supernatant liquid, no thread, easy to apply | Burgundy, supernatant liquid, no thread, very easy to apply |
| Available Iodine content | 92.9%/ 91.6%/ 94.3% | 96.9%/98.4%/ 93.1% | 95.8%/91.6%/ 94.3% |
| Sample packed in brown bottles | | | |
| Film formation time (60° C. after 10 days) | 1 min 35 s | 1 min 40 s | 1 min 15 s |
| Appearance (60° C. after 10 days) | Burgundy, supernatant liquid, no thread, easy to apply | Burgundy, supernatant liquid, no thread, easy to apply | Burgundy, supernatant liquid, no thread, very easy to apply |
| Available Iodine content | 110.2%/ 106.4%/ 114.2% | 105.9%/ 104.9%/ 108.9% | 99.6%/97.1%/ 95.8% |

NOTE:
% refers to the percentage of total formulation volume (W/W).

When choosing polyvinylbutyral (PVB) of a lower molecular weight (90,000-120,000) instead of higher molecular weight (170,000-250,000) as film-forming material, a clear and stable solution was unexpectedly obtained even without acetone as a solvent, and rapid thin-film formation was also unexpectedly achieved within 90 seconds.

Example 8. Determination of Available Iodine Amount

Titrate with 0.01044 mol/L Sodium Thiosulfate Solution:
Configuration of titration solution: 5 mL pipettes were used to pipet 5 mL 0.1044 mol/L sodium thiosulfate solution (calibrated) to a 50 mL volumetric flask, and purified water was then added to the flask to give a 0.01044 mol/L sodium thiosulfate solution.

Preparation of Samples:

A sample of 5 g was taken and ethanol was added to the sample to reach the volume of 50 mL, shake well to give a sample for titration.

Shown below in Table 8 are the available iodine amounts obtained from the Formulations that had been placed at 60° C. for 10 days are shown below in Table 8.

TABLE 8

| Stored in transparent glass bottle (T) Stored in brown glass bottle (B) | Sample Weight (g) | Volume of sodium thiosulfate (mL) | Available iodine (mg) | Available iodine content % (calculated according to 20 mg iodine in theory) |
| --- | --- | --- | --- | --- |
| Formulation53, (T) | 4.99/4.99/4.99 | 7.0/6.9/7.1 | 18.6/18.3/18.9 | 92.9/91.6/94.3 |
| Formulation53, (B) | 4.99/4.98/4.99 | 8.3/8.0/8/6 | 22.0/21.2/22.8 | 110.2/106.4/114.2 |
| Formulation54, (T) | 4.99/4.98/4.98 | 7.3/7.4/7.0 | 19.4/19.7/18.6 | 96.9/98.4/93.1 |
| Formulation54, (B) | 4.88/4.99/4.99 | 7.8/7.9/8.2 | 21.2/21.0/21.8 | 105.9/104.9/108.9 |
| Formulation58, (T) | 4.98/4.99/4.99 | 7.2/6.9/7.1 | 19.2/18.3/18.9 | 95.8/91.6/94.3 |
| Formulation58, (B) | 4.99/4.98/4.98 | 7.5/7.3/7.2 | 19.9/19.4/19.2 | 99.6/97.1/95.8 |

Example 9. Evaluation of Stability of Film-Forming PVP-I Composition after Stored at 37° C. for 3 Months The following three PVP-I liquid bandage compositions of this invention were used in evaluation of their stability after they were stored at 37° C. for 3 months: (1) Sample 1: PVB 8%, MW: 90,000-120,000, PVP-I 2%; (2) Sample 2: PVB 8%, MW: 90,000-120,000 W, PVP-I 1%; and (3) Sample 3: PVB 8%, MW: 9-12 W, PVP-I 0.5%)

The concentration of available iodine, viscosity and set time (time to dry when applying the liquid bandage on skin) were measured and recorded in Tablet 9. Test samples were made and tested in triplets.

TABLE 9

The Stability of PVP-I Film-forming Compositions stored at 37° C. for 3 months

| | Available Iodine $I_d$ (mg) | Viscosity (CP) | Set time (seconds) |
| --- | --- | --- | --- |
| 0 day | | | |
| Samples 1-1 | 21.64 | 118.4 | 101 |
| Samples 1-2 | 20.56 | 105.7 | 95 |
| Samples 1-3 | 19.89 | 112.5 | 80 |
| Average | 20.70 | 112.2 | 93 |
| Samples 2-1 | 12.88 | 105.7 | 83 |
| Samples 2-2 | 12.73 | 120.6 | 76 |
| Samples 2-3 | 11.69 | 124.7 | 96 |
| Average | 12.4 | 117.0 | 85 |
| Samples 3-1 | 5.53 | 119.8 | 85 |
| Samples 3-2 | 5.04 | 105.8 | 90 |
| Samples 3-3 | 5.13 | 114.8 | 105 |
| Average | 5.23 | 113.5 | 93 |
| 1 month at 37° C. | | | |
| Samples 1-1 | 17.98 | 115.7 | 83 |
| Samples 1-2 | 20.62 | 136.4 | 102 |
| Samples 1-3 | 20.61 | 105.9 | 90 |
| Average | 19.74 | 119.3 | 92 |
| Samples 2-1 | 11.51 | 99.4 | 109 |
| Samples 2-2 | 10.71 | 106.5 | 88 |
| Samples 2-3 | 10.31 | 123.6 | 96 |
| Average | 10.84 | 109.8 | 98 |
| Samples 3-1 | 3.26 | 118.6 | 84 |
| Samples 3-2 | 4.27 | 121.5 | 107 |
| Samples 3-3 | 6.11 | 105.5 | 108 |
| Average | 4.54 | 115.2 | 100 |
| 2 month at 37° C. | | | |
| Samples 1-1 | 19.08 | 120.1 | 76 |
| Samples 1-2 | 20.42 | 97.9 | 89 |
| Samples 1-3 | 18.61 | 112..9 | 85 |
| Average | 19.37 | 109.0 | 83 |
| Samples 2-1 | 10.54 | 130.7 | 96 |
| Samples 2-2 | 9.98 | 125.7 | 103 |
| Samples 2-3 | 10.69 | 106.8 | 97 |
| Average | 10.4 | 121.1 | 99 |
| Samples 3-1 | 3.19 | 97.8 | 105 |
| Samples 3-2 | 2.76 | 103.7 | 89 |
| Samples 3-3 | 3.47 | 114.9 | 98 |
| Average | 3.14 | 105.5 | 97 |
| 3 month at 37° C. | | | |
| Samples 1-1 | 19.47 | 125.9 | 108 |
| Samples 1-2 | 18.06 | 108.9 | 115 |
| Samples 1-3 | 21.43 | 119.6 | 96 |
| Average | 19.65 | 118.1 | 106 |
| Samples 2-1 | 10.13 | 105.7 | 86 |
| Samples 2-2 | 10.17 | 129.5 | 100 |
| Samples 2-3 | 10.27 | 110.5 | 94 |
| Average | 10.19 | 115.2 | 93 |
| Samples 3-1 | 2.89 | 97.0 | 93 |
| Samples 3-2 | 3.23 | 103.6 | 81 |
| Samples 3-3 | 3.80 | 120.9 | 94 |
| Average | 3.31 | 107.2 | 89 |

TABLE 10

Comparison of Stability of different concentration of PVP-I Film-Forming Compositions after being stored at 37° C. for 3 months (assuming 0 day data as 100%)

|  | 0 day | 1 month | | 2 months | | 3 months | |
|---|---|---|---|---|---|---|---|
| Available Iodine Id (mg) | | | | | | | |
| Sample 1 | 20.7 | 19.74 | 95.36% | 19.37 | 93.57% | 19.65 | 94.93% |
| Sample 2 | 12.4 | 10.84 | 87.42% | 10.4 | 83.87% | 10.19 | 82.18% |
| Sample 3 | 5.23 | 4.54 | 86.81% | 3.14 | 60.04% | 3.31 | 63.29% |
| Viscosity (CP) | | | | | | | |
| Sample 1 | 112.2 | 119.3 | 106.33% | 109 | 97.15% | 118.1 | 105.26% |
| Sample 2 | 117 | 109.8 | 93.85% | 121.1 | 103.50% | 115.2 | 98.46% |
| Sample 3 | 113.5 | 115.2 | 101.50% | 105.5 | 92.95% | 107.2 | 94.45% |
| Set Time (second) | | | | | | | |
| Sample 1 | 93 | 92 | 98.92% | 83 | 89.25% | 106 | 113.98% |
| Sample 2 | 85 | 98 | 115.29% | 99 | 116.47% | 93 | 109.41% |
| Sample 3 | 93 | 100 | 107.53% | 97 | 104.30% | 89 | 95.70% |

The concentrations of available iodine content reduced from 20.70 mg to 19.65 mg, a 5.1% reduction after Sample 1 (PVB 8%, MW: 9-12 W, PVP-I 2%) had been stored at 37° C. for 3 months, and sample2 (PVB 8%, MW: 9-12 W, PVP-I 1%) had a 17.8% reduction (12.4 mg to 10.19 mg), sample3 (PVB 8%, MW: 9-12 W, PVP-I 0.5%) had a 36.7% reduction in three test groups, which indicated that the 2% povidone iodine containing sample was preferable choice. The viscosity and set time of the three samples did not change significantly.

Example 10. Additional Examples of Thin-Film Forming PVP-I Compositions

Additional examples of thin-film forming PVP-I compositions were prepared to include the following ingredients: povidone Iodine (0.5% to 2.5%), polyvinylbutyral (5% to 10%), ethanol (50% to 60%), ethyl acetate (8% to 10%), acetone (20% to 25%) (optional), castor oil (0.1% to 1%), and camphor (1% to 2%) (optional).

Example 11. PVP-I Film-Forming Spray Preparation 0.8 g of PVB of a molecular weight 90,000-120,000, 6.75 g of ethyl alcohol absolute, 2.2 g of ethyl acetate, 0.05 g of castor oil, 0.2 g of PVP-I, and a suitable amount of difluormethane were mixed together and vigorously stirred until PVP-I was dissolved. The solution was filled into spray apparatus as PVP-I Film-Forming Spray.

Example 12. Demonstration of Film-Forming Process

A PVP-I Film-Forming composition of this invention was applied on human skin, and the film-forming process was observed. The solvent completely evaporated from the composition and resulted in a thin film on the skin within 2 minutes. The film was continuous and adhesive, and it stuck to the skin and was hard to be scraped off under water rinse.

Example 13. Film-Forming Compositions Containing 2% Chlorhexidine Digluconate (CHG)

Film-forming liquid bandage formulations of this invention containing 2% CHG were prepared according to formulations set forth below in Table 11.

TABLE 11

Film-Forming Chlorhexidine Compositions

| Film-forming materials | Polyvinylbutyral |
|---|---|
| | Nitrocellulose |
| Solvents | Ethanol or isopropanol |
| | Ethyl acetate |
| | Acetone |
| | Butyl acetate |
| | Caster oil |
| Chlorhexidine digluconate | 2% |

Example 14. Film-Forming Composition Containing 0.5% Chlorhexidine Digluconate A film-forming liquid bandage composition containing 0.5% chlorhexidine digluconate (CHG) was prepared according to formulation set forth below in Table 12. The CHG composition was applied to the skin and quickly formed a film under 30 seconds.

TABLE 12

| Film-forming material | Polyvinylbutyral 6% |
|---|---|
| Solvent | Ethanol 92% |
| | Caster oil 1.5% |
| Chlorhexidine digluconate | 0.5% |

Example 15. A Film-Forming Composition Containing 0.5% Octenidine Dihydrochloride A film-forming liquid bandage composition containing 0.5% octenidine dihydrochloride (by weight) was prepared according to formulation set forth below in Table 13. The octenidine dihydrochloride film-forming composition was applied to the skin and quickly formed a thin film under 30 seconds.

TABLE 13

| Film-forming material | Polyvinylbutyral 6% |
|---|---|
| Solvent | Ethanol 92% |
| | Caster oil 1.5% |
| Octenidine dihydrochloride | 0.5% |

Example 16. In Vitro Release Test of PVP-I Film-Forming Composition

A transdermal diffusion apparatus (Franz single-room diffusion cell) shown in FIG. 1 was used to investigate the drug release properties of PVP-I film-forming compositions of this invention, and PVP-I film-forming composition's sustained release function was assessed by measuring the rate of drug diffusion through a semi-permeable membrane with non-barrier properties and reach the receiving media according to the following procedure.

First, 50 g PVP-I film-forming composition (liquid Bandage) was added to the supply cell (Up Cell), and the solvent was allowed to evaporate to form thin films. A PVP-I solution of the same PVP-I concentration was used as a positive control, and in accordance to the available iodine 0.1 g sample configuration, to fill in the supply cell.

A dialysis membrane (soaked with purified water) of a suitable size was then placed between the receiving cell (Down Cell) and supply cell. A magnetic stirrer was put in the receiving cell. Purified water was used as release medium, and the temperature was set at 32° C. Purified water was added as release medium from the sampling port, and brought into contact with a dialysis membrane. The diffusion cell was placed in a 32° C. water bath, and a magnetic stirrer was turned on. At time intervals 5 minutes, 30 minutes, 60 minutes, 120 minutes, 4 hours, 8 hours, 12 hours, 18 hours, 24 hours, 36 hours, and 48 hours, all the liquid in the receiving cell was removed, and the samples were supplemented with an equal amount purified water at the same temperature. The concentration of available iodine was measured as described below to calculate the cumulative drug release amount.

Measurement of Concentration of Available Iodine 5 mL of a sodium thiosulfate standard solution (0.1044 mol/L) was pipetted to a 50 mL volumetric flask, and then deionized water was added to the sodium thiosulfate solution to the total volume of 50 mL.

Figure 2:
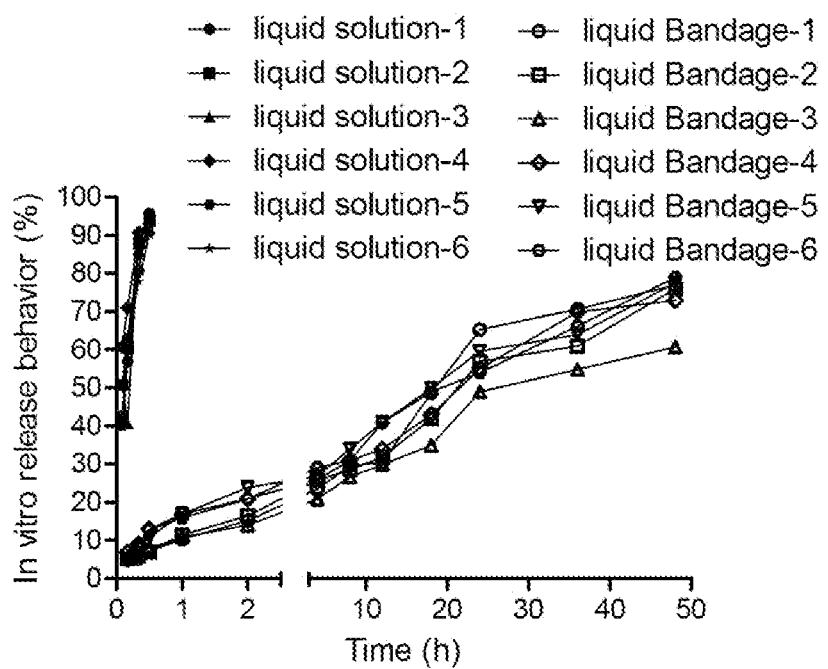
FIG. 2 shows iodine release profiles from PVP-I-containing thin film-forming compositions of this invention, as reflected by the amounts of available iodine.

5 g of a test sample was added into a 100 mL beaker and ethanol was added to the beaker for the total weight of 50 g, and the mixture was stirred and mixed well. The sample was titrated to colorless by the sodium thiosulfate solution just prepared, and the volume of the sodium thiosulfate solution consumed was recorded. The volume amount was used for calculating then iodine content based on the following equation:

$$I_d = \Delta V \times 0.01044 \times 12.69 \times 10/(0.1 \times Ws)$$

wherein, $I_d$ is the content of iodine in 10 g liquid bandage composition sample at different test times, $\Delta V$ is the volume of sodium thiosulfate solution consumed, and Ws is the weight of the sample. 6 samples of each composition were used to obtain the average amount of available iodine. The release profiles of iodine from PVP-I film-forming composition (liquid bandage), as reflected by the amounts of available iodine, are shown in FIG. 2. As shown in FIG. 2, approximately 92.89±2.14% of iodine was released from the solution samples within half an hour. By comparison, the release of iodine were 73.83±6.72% from the film-forming composition samples (n=6) after 48 hours, which indicated that the film-forming PVP-I compositions of this invention provided sustain release of iodine. In fact, it was surprisingly and unexpectedly discovered that film-forming PVP-I compositions of this invention had achieved a much slower release of iodine comparing to the same concentration of PVP-I solution.

Example 17. Film-Forming Compositions In Vivo Efficacy Experiments

To evaluate in vivo efficacy of film-forming compositions of this invention against bacteria on the wound, ICR mice were used animal model. Man-made wounds were infected with bacteria. Four treatment groups with PVP-I film-forming compositions, SurgiSeal® skin adhesive, NewSkin® liquid bandage, and CHG film-forming composition, were studied. *Staphylococcus aureus, Escherichia coli* and *Pseudomonas aeruginosa* bacteria, $5*10^7$ CFU/ml, 1:1:1 were mixed to make bacteria solution.

Animals 18-20 g ICR mice were randomly divided into four groups of 10. Artificially scraped off hair on the abdomen and back, to show bare skin. A knife was used to draw 2-3 cm length wound, with depth to the dermis (bleeding so far). All wounds were infected with mixed bacterial, and set aside.

Figure 3:
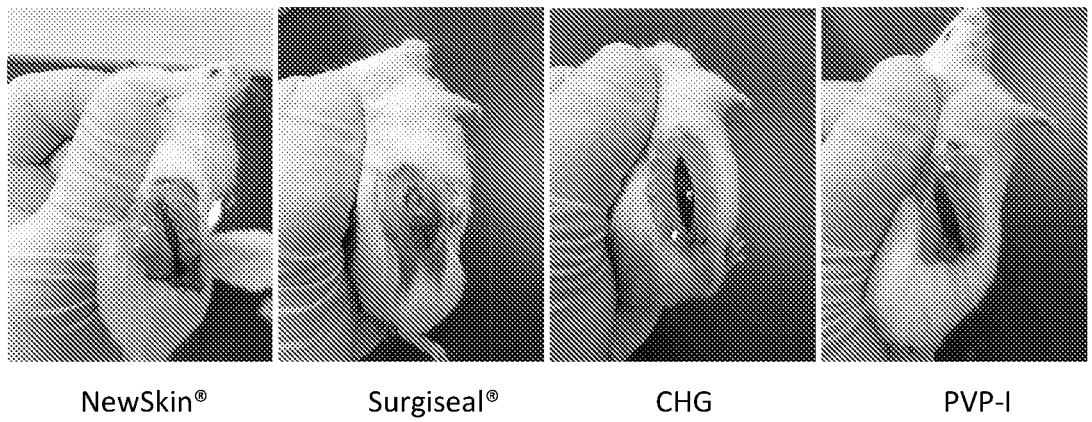
FIG. 3 (including FIGS. 3A1-3E4) shows pictures to show skin treatment effects of different agents (including two compositions of this invention) on mice.
Figure 3:
Figure 3:
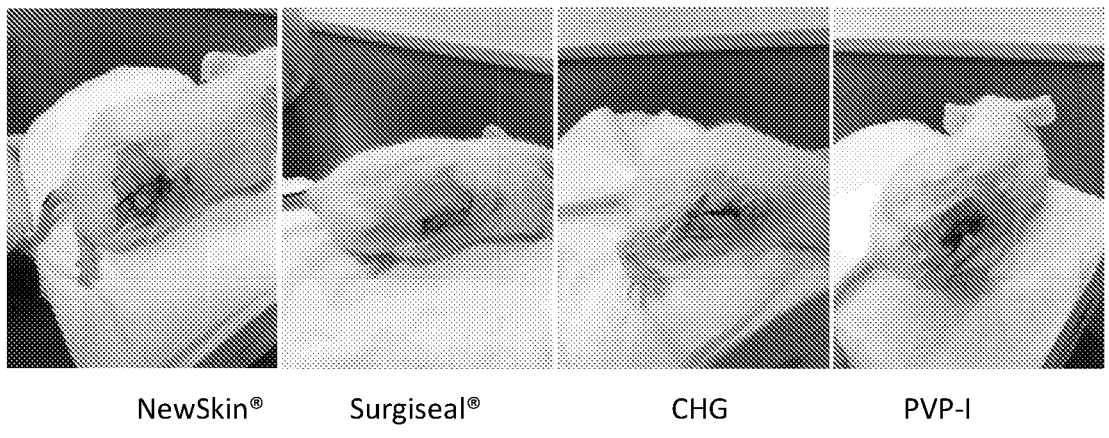
Figure 3:
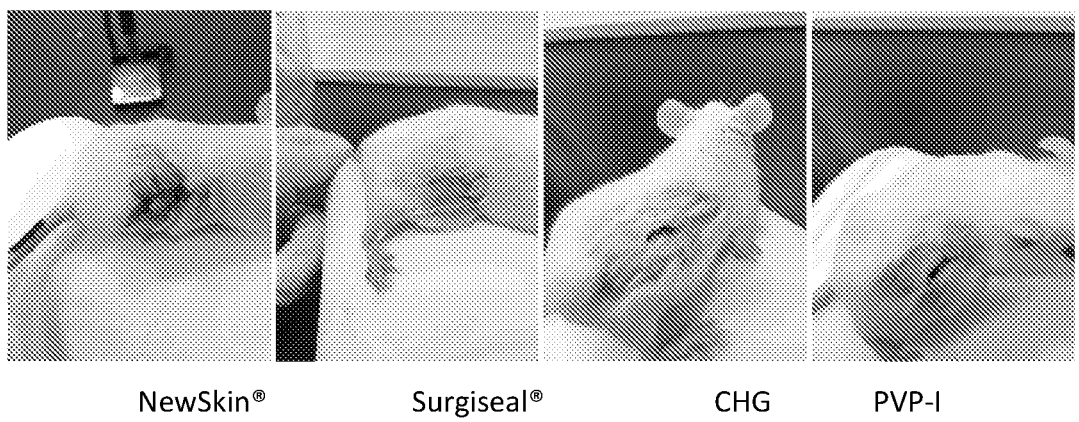
Figure 3:
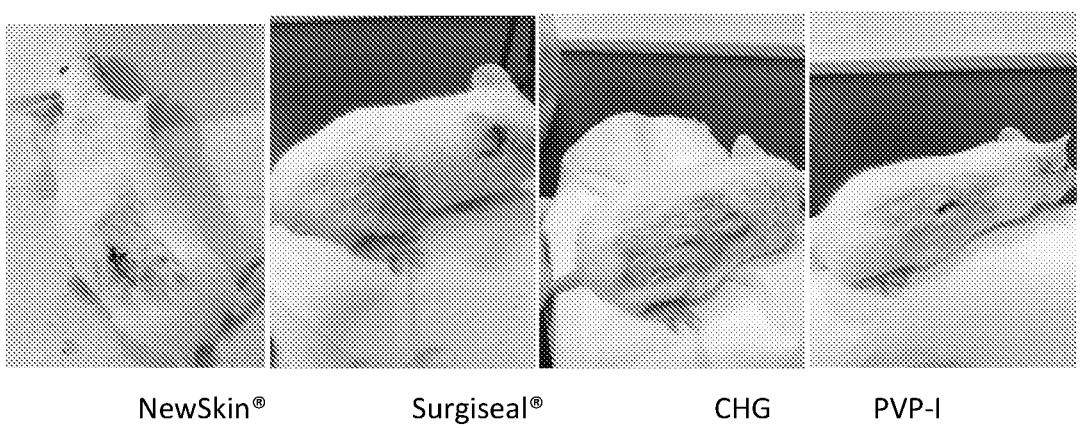

Study Procedure:

PVP-I film-forming composition, CHG film-forming composition, SurgiSeal® skin adhesive, and NewSkin® liquid Bandages were used as four treatment groups to treat the wound infections, continuous treatment for eight days, respectively. At 0 Day, 2 Day, 4 Day, 6 Day, 8 Day after the beginning of the treatments, the wound healing was observed, the wound lengths were measured, and the wounds were photographed. FIG. 3, including all the sub-figures, include the pictures showing the wounds at different stages of the healing.

Assessment of Efficacy

Evaluate wound healing effect using a scoring system and Table 14 is a score shoot from the test.

TABLE 14

| | No (10-8 pts), Mild (7-5 pts), Moderate (4-2pts), Severe (0-1pts) | | | |
|---|---|---|---|---|
| Items | NewSkin ® | Surgiseal ® | CHG | PVP-I |
| Inflamed wound | | | | |
| Redness and | 8/7/9/9/8 | 9/8/9/9/9/ | 10/9/10/10/10 | 10/9/10/10/10 |
| swollen | 8/7/8/8/9 | 10/10/10/10/10 | 9/10/10/10/10 | 9/10/10/10/10 |
| Tissue fluid | 7/7/8/7/8 | 7/7/8/8/9 | 10/9/10/10/10 | 10/9/10/10/10 |
| exudation | 9/7/8/9/8 | 10/10/10/10/10 | 9/10/10/10/10 | 9/10/10/10/10 |
| Concurrent | 10/10/10/10/10 | 10/9/10/10/10 | 10/9/10/10/10 | 10/9/10/10/10 |
| infection | 10/10/10/10/10 | 9/10/10/10/10 | 9/10/10/10/10 | 9/10/10/10/10 | n = 10

Observations:

For the mice group which received NewSkin® spraying liquid bandage treatment, the wound was not closed in the next day, and tissue fluid leaked out (2 Days, circle). On day 4, wound was healed, tissue has grown normally, and no inflammation was observed and no tissue fluid leaked out.

For the mice group which received Surgiseal® skin adhesive treatment, tissue fluid leaking was observed in the next day (2 D, circle and arrow), and remaining mice's wounds healed normally, no tissue fluid leaked out.

For the mice group which received PVP-I film-forming composition and CHG film-forming composition treatment, wound was healed fully in the next day, and no inflammation was observed and no tissue fluid linking out.

Based on clinical observations after the treatment, the wounds of the four groups of mice received treatment all have been healed. During the early wound healing period, the mice groups received PVP-1 film-forming composition and CHG film-forming composition treatment, wounds were healed faster. The mice groups received NewSkin® spraying liquid bandage and Surgiseal® skin adhesive appeared tissue fluid exudation, respectively. PVP-I film-forming composition and CHG film-forming composition unexpectedly provided much better results for the wound healing.

Example 18. PVP-I Film-Forming Composition In Vitro Safety Studies

Following the protocol described in ISO 10993-5:2009 "Biological evaluation of medical devices—Part 5: In vitro cytotoxicity tests", safety of PVP-I film-forming composition was tested in vitro.

Cell Line and Culture

NCTC clone 929 (L cell, L-929, derivative of Strain L) was purchased from TongpaiBio (Shanghai, China). The cells were incubated in Dulbecco minimum essential medium (DMEM) with 10% FBS in an incubator at 37±2° C. under an atmosphere of 5% $CO_2$ for 24 hours before extracts addition. The medium was supplemented with 100 U/mL penicillin and 100 mg/mL streptomycin.

Procedure

Extract preparation: Take PVP-I film-forming composition 0.5 g and let solvent evaporate to form films. Then a 2×3 cm film was made and incubated at 37° C. for 24 hours within 2 mL DMEM (area/medium=6 $cm^2$/mL). And extracts from film-forming composition without PVP-I were also made as above-mentioned procedure. Blank DMEM and blank extracts are used as control groups. All the extraction was filtered with a 0.22 μm membrane before adding into cell.

L929 cells at a density of 1×104 cell/well were seeded and incubated in 96-well (100 μl/well) plates for 24 hours at 37° C. under an atmosphere of 5% $CO_2$. Then cells were incubated with different extracts (extracts of PVP-I film, extracts of film-forming composition without PVP-I, 100 μl/well), and blank DMEM were used as control. After incubation for 24 hours, 150 μL culture medium was sucked away and 50 μL of Cell Titer-Glo® (Promega) was added for assay the luminescence cell viability using PHERAstar FS (BMG LABTECH).

Assay was repeated two times (n=18/time) to get the average reading, the cell viability calculated according to the following formula:

$$\text{Cell viability}(\%) = \frac{OD_s}{OD_{control}} \times 100\%$$

wherein $OD_s$ is the luminescence value of samples and $OD_{control}$ is the luminescence value of blank DMEM.

3) Safety Assessment Criteria:

24 hours survival rate of more than 70% is regarded as safe. The safety profile of povidone iodine film-forming compositions was assessed and the result is shown in Table 15.

TABLE 15

| Assay 1 | | | | |
|---|---|---|---|---|
| Blank DMEM | Extract 1 | Extract 2 | Extract 3 | Extract from Film-Forming Composition without PVP-I |
| 852886.8 | 800044.8 | 827177.8 | 827092.8 | 871900.8 |
| 880748.8 | 810540.8 | 830208.8 | 844111.8 | 885312.8 |
| 874190.8 | 804865.8 | 813113.8 | 823774.8 | 882971.8 |
| 891359.8 | 822358.8 | 883837.8 | 850115.8 | 865010.8 |
| 846232.8 | 809251.8 | 818471.8 | 813862.8 | 855490.8 |
| 873706.8 | 838540.8 | 850548.8 | 867328.8 | 872844.8 |
| Average: 869854.3 | 814267.1 | 837226.5 | 837714.5 | 872255.3 |
| Cell viability (%) | 93.6% | 96.2% | 96.3% | 100.3% |

| Assay 2 | | | | |
|---|---|---|---|---|
| Blank | Samples 1 | Samples 2 | Samples 3 | Extract from Film-Forming Composition without PVP-I |
| 808188 | 873154 | 760355 | 800970 | 818684 |
| 835321 | 879313 | 762449 | 822593 | 838352 |
| 835236 | 924671 | 861030 | 919579 | 852255 |
| 828021 | 880044 | 846684 | 786511 | 813009 |
| 878662 | 894107 | 858692 | 785583 | 821257 |
| 907947 | 890392 | 875472 | 828260 | 831918 |
| Average: 848895.8 | 890280.2 | 827447 | 823916 | 829245.8 |
| Cell viability (%) | 104.9% | 97.5% | 97.1% | 97.7% |

The safety/toxicity of PVP-I film-forming compositions passed the safety requirements.

Example 19. Anti-Bacterial Efficacy of PVP-I Film-Forming Composition

Surface Time Kill study where bacteria (1×108 CFU) were placed on top of dried films (test substances), the speed of the microbicidal activity was measured using a select battery of microorganisms including antibiotic resistant organisms. The contact time was selected at 1, 15, and 60 minutes, respectively. The following microorganisms *Escherichia coli* ATCC #8739, *Klebsiella pneumoniae* ATCC #4352, *Staphylococcus epidermidis* ATCC #12228, and *Staphylococcus aureus* (MRSA) ATCC #33592 were selected as test microorganism(s) by the microbiology lab-Microchem Laboratory in Texas, USA.

Test Method: ASTM International Method E1153, Surface Time Kill

Summary of the Procedure

The test microorganism was prepared, usually by growth in liquid culture medium. The test culture may be supplemented with an artificial soil load, such as horse or fetal bovine serum, for one-step cleaner/sanitizer claims.

Sterilized carriers were inoculated with a volume of the test culture. Inoculated slides were dried in an incubator. Only completely dried carriers were used in the test.

Test carriers were treated with the test substance and incubated for the predetermined contact time.

Control carriers were treated with a buffered saline solution and were allowed to sit for the predetermined contact time.

At the conclusion of the contact time, test and control carriers were chemically neutralized. Dilutions of the neutralized test substance were evaluated using appropriate growth media to determine the surviving microorganisms at the respective contact time.

The effect of the test substance was compared to the effect of the control substance in order to determine microbial reductions.

Passing Criteria

ASTM International defines passing criteria to be a 3 Log 10 or 99.9% reduction in the treated test carriers when compared to the control carriers.

Testing Parameters Used in the Study

| | |
|---|---|
| Test Carrier Size: 1 inch × 2 inch | Replicates: Triple |
| Test Substance Volume: 3.0 mL | |
| Culture Growth Media: Tryptic Soy Broth | Culture Growth Time: 18-24 hours |
| Culture Supplement: None | Carrier Inoculum Volume: 0.020 ml |
| Inoculum Concentration: 1 × 108 CFU/ml | Carrier Inoculum Area: 1 inch × 2 inch |
| Carrier Dry Temp: 25° C. ± 2° C. | Carrier Dry Time: <15 minutes |
| Contact Temp.: Ambient (25° C. ± 2° C.) | Contact Humidity: Ambient |
| Contact Time: 1 min, 15 min, 1 hr | Neutralizer: D/E Neutralizing Broth |
| Enumeration Plate 36° C. ± 1° C. Incubation Temperature: | Enumeration Plate 24-48 hours Incubation Time: |
| Incubation Conditions: Aerobic | |

Study Modifications

Test carriers for this testing were ~1"×2" surfaces of rehydrated VITRO-SKIN. VITRO-SKIN was rehydrated as per Sponsor's instructions ~18 hours prior to conducting testing.

Study Notes

To evaluate the viability of the test microorganism following the 1-hour contact time, 3.0 mL Phosphate Buffered Saline (PBS) was applied to inoculated test surfaces as a control.

Test carriers were spot inoculated with 0.020 mL test inoculum due to the VITRO-SKIN sticking and tearing when a spreader was used.

Control Results

Neutralization Method: Validated Media Sterility: Sterile Growth Confirmation: Confirmed, Morphology on TSA Calculations $$\text{Percent Reduction} = \left(\frac{B-A}{B}\right) \times 100$$

wherein:

B=Number of viable test microorganisms on the control carriers after the contact time A=Number of viable test microorganisms on the test carriers after the contact time $$\text{Log}_{10}\text{Reduction} = \text{Log}\left(\frac{B}{A}\right)$$

wherein:

B=Number of viable test microorganisms on the control carriers after the contact time A=Number of viable test microorganisms on the test carriers after the contact time Results of the Study

TABLE 16

Results for *E. coli* 8739

| Test Microorganism | Test Substance | Contact Time | Replicate | Replicate CFU/carrier | Average CFU/carrier | Percent Reduction vs. Time Zero Control | Log10 Reduction vs. Time Zero Control |
|---|---|---|---|---|---|---|---|
| *E. coli* 8739 | PBS (Control Substance) | Time Zero (i.e. Initial Numbers Control) | 1 | 2.60E+06 | 1.83E+06 | N/A | |
| | | | 2 | 6.80E+05 | | | |
| | | | 3 | 2.20E+06 | | | |
| | | 60 min | 1 | 4.50E+05 | 7.07E+05 | | |
| | | | 2 | 7.80E+05 | | | |
| | | | 3 | 8.90E+05 | | | |
| | PVB 6% PVPI 2% | 1 min | 1 | <5 | <5 | >99.9997% | >5.56 |
| | | | 2 | <5 | | | |
| | | | 3 | <5 | | | |
| | | 15 min | 1 | <5 | <5 | >99.9997% | >5.56 |
| | | | 2 | <5 | | | |
| | | | 3 | <5 | | | |
| | | 60 min | 1 | <5 | <5 | >99.9997% | >5.56 |
| | | | 2 | <5 | | | |
| | | | 3 | <5 | | | |

Figure 4:
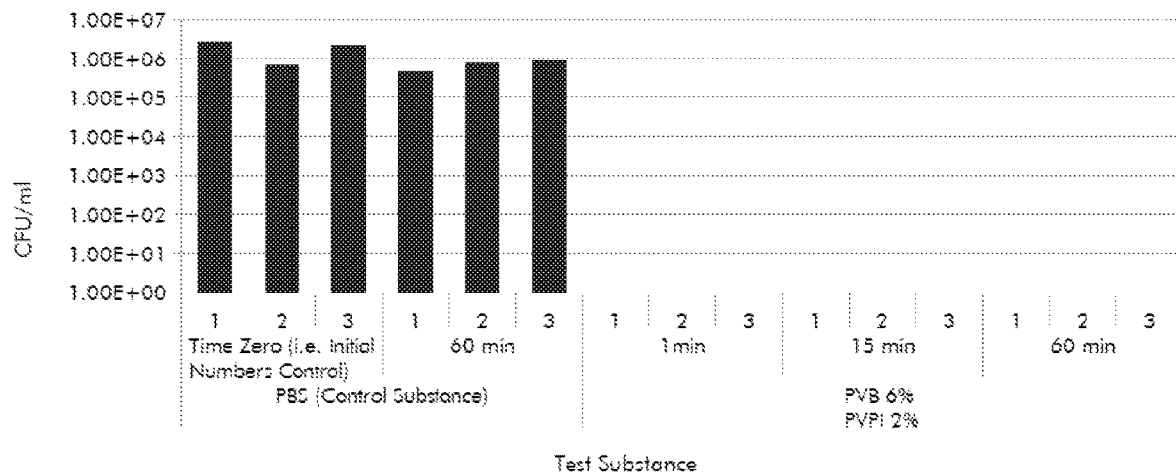
FIG. 4 shows a graph regarding test results for *E. coli* 8739.

The test results for *E. coli* 8739 are shown in the table above and FIG. 4. The limit of detection for this assay was 5 CFU. Non-detects are represented as zero in the graph in FIG. 4.

TABLE 17

Results for *K. pneumoniae* 4352

| Test Microorganism | Test Substance | Contact Time | Replicate | Replicate CFU/carrier | Average CFU/carrier | Percent Reduction vs. Time Zero Control | Log10 Reduction vs. Time Zero Control |
|---|---|---|---|---|---|---|---|
| *K. pneumoniae* 4352 | PBS (Control Substance) | Time Zero (i.e. Initial Numbers Control) | 1 | 2.10E+06 | 2.57E+06 | N/A | |
| | | | 2 | 3.40E+06 | | | |
| | | | 3 | 2.20E+06 | | | |
| | | 60 min | 1 | 1.26E+05 | 4.55E+05 | | |
| | | | 2 | 3.30E+05 | | | |
| | | | 3 | 9.10E+05 | | | |
| | PVB 6% PVPI 2% | 1 min | 1 | <5 | <5 | >99.9998% | >5.71 |
| | | | 2 | <5 | | | |
| | | | 3 | <5 | | | |
| | | 15 min | 1 | <5 | <5 | >99.9998% | >5.71 |
| | | | 2 | <5 | | | |
| | | | 3 | <5 | | | |
| | | 60 min | 1 | <5 | <5 | >99.9998% | >5.71 |
| | | | 2 | <5 | | | |
| | | | 3 | <5 | | | |

Figure 5:
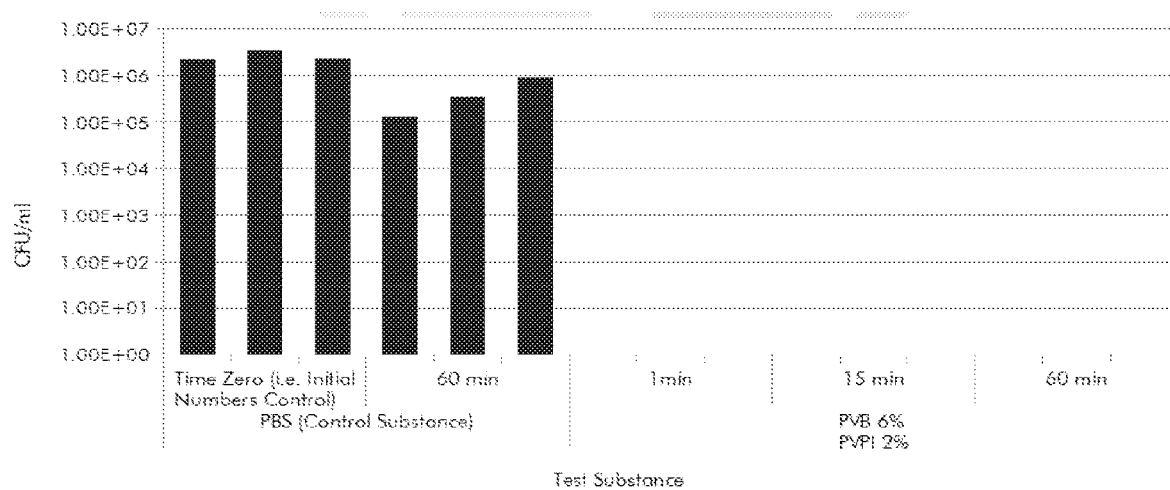
FIG. 5 shows a graph regarding test results for *K. pneumoniae* 4352.

The test results for *K. pneumoniae* 4352 are shown in the table above and FIG. 5. The limit of detection for this assay was 5 CFU. Non-detects are represented as zero in the graph in FIG. 5.

TABLE 18

Results for *S. epidermidis* 12228

| Test Microorganism | Test Substance | Contact Time | Replicate | Replicate CFU/carrier | Average CFU/carrier | Percent Reduction vs. Time Zero Control | Log10 Reduction vs. Time Zero Control |
|---|---|---|---|---|---|---|---|
| *S. Epidermidis* 12228 | PBS (Control Substance) | Time Zero (i.e. Initial Numbers Control) | 1 | 6.70E+06 | 1.48E+07 | N/A | |
| | | | 2 | 2.27E+07 | | | |
| | | | 3 | 1.51E+07 | | | |
| | | 60 min | 1 | 1.90E+06 | 3.27E+06 | | |
| | | | 2 | 2.60E+06 | | | |
| | | | 3 | 5.30E+06 | | | |
| | PVB 6% PVPI 2% | 1 min | 1 | <5 | <5 | >99.9997% | >6.47 |
| | | | 2 | <5 | | | |
| | | | 3 | <5 | | | |
| | | 15 min | 1 | <5 | <5 | >99.9997% | >6.47 |
| | | | 2 | <5 | | | |
| | | | 3 | <5 | | | |
| | | 60 min | 1 | <5 | <5 | >99.9997% | >6.47 |
| | | | 2 | <5 | | | |
| | | | 3 | <5 | | | |

Figure 6:
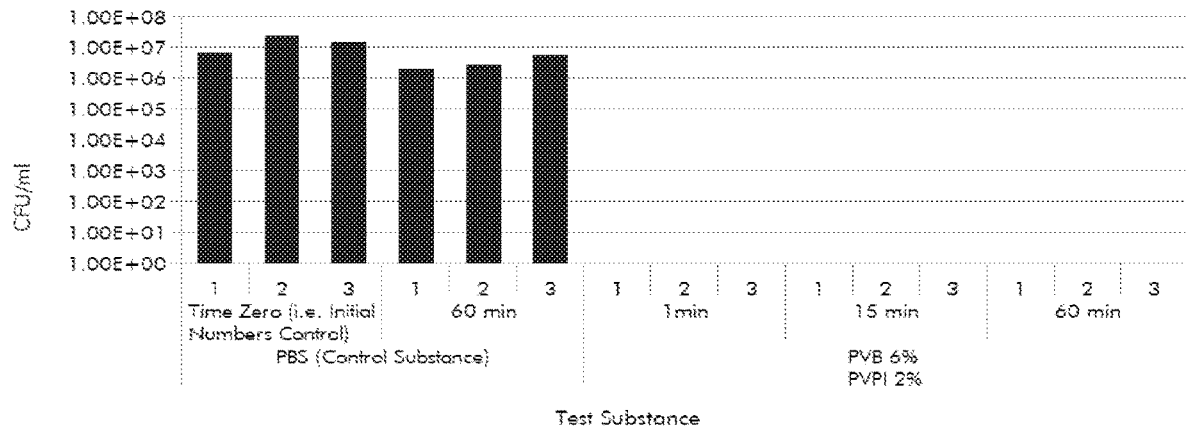
FIG. 6 shows a graph regarding test results for *S. epidermidis* 12228.

The test results for *S. epidermidis* 12228 are shown in the table above and FIG. 6. The limit of detection for this assay was 5 CFU. Non-detects are represented as zero in the graph in FIG. 6.

TABLE 19

Results for *S. aureus* 33592

| Test Microorganism | Test Substance | Contact Time | Replicate | Replicate CFU/carrier | Average CFU/carrier | Percent Reduction vs. Time Zero Control | Log10 Reduction vs. Time Zero Control |
|---|---|---|---|---|---|---|---|
| *S. aureus* 33592 | PBS (Control Substance) | Time Zero (i.e. Initial Numbers Control) | 1 | 1.71E+07 | 1.39E+07 | N/A | |
| | | | 2 | 1.60E+07 | | | |
| | | | 3 | 8.60E+06 | | | |
| | | 60 min | 1 | 5.30E+06 | 6.30E+06 | | |
| | | | 2 | 5.50E+06 | | | |
| | | | 3 | 8.10E+06 | | | |
| | PVB 6% PVPI 2% | 1 min | 1 | <5 | <5 | >99.9996% | >6.44 |
| | | | 2 | <5 | | | |
| | | | 3 | <5 | | | |
| | | 15 min | 1 | <5 | <5 | >99.9996% | >6.44 |
| | | | 2 | <5 | | | |
| | | | 3 | <5 | | | |
| | | 60 min | 1 | <5 | <5 | >99.9996% | >6.44 |
| | | | 2 | <5 | | | |
| | | | 3 | <5 | | | |

Figure 7:
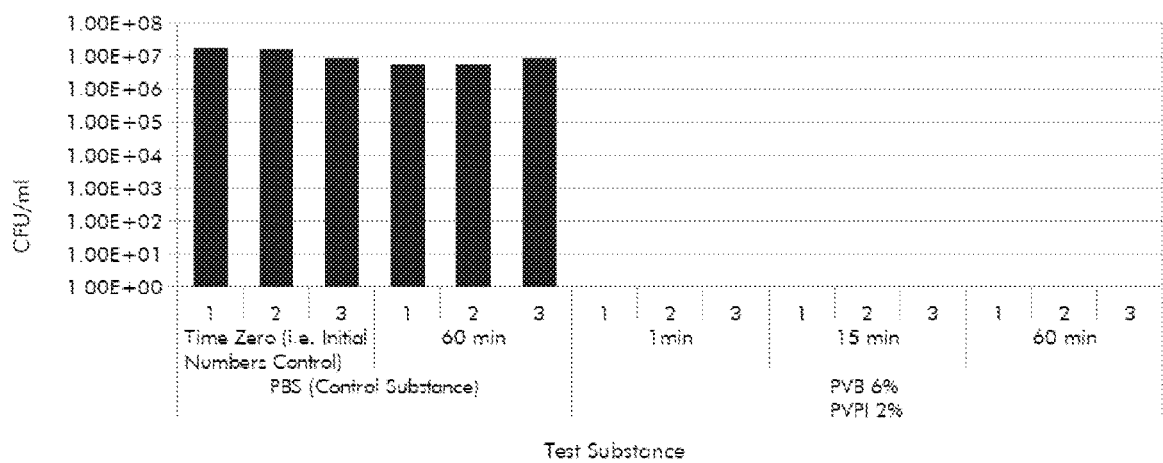
FIG. 7 shows a graph regarding test results for *S. aureus* 33592.

The test results for *S. aureus* 33592 are shown in the table above and FIG. 7. The limit of detection for this assay was 5 CFU. Non-detects were represented as zero in the graph in FIG. 7.

Conclusion:

More than 5 Log 10 or 99.999% microbial reduction in the treated test carrier (PVP-I film-forming composition) against all three selected microorganisms *Escherichia coli* ATCC #8739, *Klebsiella pneumoniae* ATCC #4352, *Staphylococcus epidermidis* ATCC #12228, and *Staphylococcus aureus* (MRSA) ATCC #33592 when compared to the control carriers.

Example 20. Combination of Antiseptics and Cyanoacrylates as Film-Forming Compositions The Povidone Iodine film-forming composition was mixed with butyl cyanoacrylate, a clear solution was obtained and the set time of the film was reduced within 30 seconds.

In another embodiment, the film-forming composition can be employed as a solution, cream, a gel, or an ointment, an emulsion, or a spray on the wound to form a rapid-deposition thin-film on the skin.

The compositions are useful for the treatment and prevention of infections in wounds, ulcers, cuts and burns; for the treatment of infections in decubitus ulcers and stasis ulcers. The compositions are suitable as a treatment against infections from bacterial, mycobacterial, viral, fungal, or amoeba causes, as well as treatment to prevent such infections in appropriate clinical settings.

The compositions are useful as skin preparations before and/or after surgical operations as disinfectants.

The invention has been described herein by reference to certain preferred embodiments. However, as obvious variations thereof will become apparent to those skilled in the art, the invention is not to be considered as limited thereto. All patents, patent applications, and references cited anywhere is hereby incorporated by reference in their entirety.

What is claimed is:

1. A non-aqueous thin-film forming composition comprising an antiseptic, a non-aqueous solvent, and a film-forming material dissolved in the non-aqueous solvent, wherein the composition is free of polyvinyl alcohol and yields a continuous and flexible protective film upon substantial removal of the solvent; the antiseptic is povidone iodine (PVP-I); and the film-forming material is polyvinylbutyral (PVB).

2. The thin-film forming composition of claim 1, wherein the antiseptic is contained in the composition at a concentration between 0.01% and 10%, between 0.1% and 2.5%, between 0.1% and 2.0%, or between 0.5% and 2.0% (weight/weight or weight/volume).

3. The thin-film forming composition of claim 1, wherein the film-forming material is contained in the composition at a concentration between 1% and 20%, or between 5% and 10% (weight/weight or weight/volume).

4. The thin-film forming composition of claim 1, further comprising ethanol, propanol, isopropanol, isopentane, ethyl acetate, acetone, or a combination thereof.

5. The thin-film forming composition of claim 1, further comprising a cooling agent, a lubricant, an antimicrobial preservative, a co-solvent, a surfactant, a viscosity builder agent, or a bioadhesive agent.

6. The thin-film forming composition of claim 5, wherein the cooling agent comprises camphor, borneol, menthol, methone glycerin acetyl ester, methone glycerin ester, methone glycerin carboxamide, methane glycerol ketal, alkyl-substituted urea, sulfonamide, terpene analog, furanone, or phosphine oxide.

7. The thin-film forming composition of claim 5, wherein the lubricant comprises propylene glycol, glycerin, blended polyvinyl alcohol, polyethylene glycol 400, light mineral oil, castor oil, hydroxypropyl methylcellulose, hypromellose, Carbopol 980, white petrolatum, soy lecithin, sodium carboxyl methylcellulose, hydroxypropyl methylcellulose, hypromellose, or a combination thereof.

8. The thin-film forming composition of claim 5, wherein the antimicrobial preservative comprises benzalkonium chloride, thimerosal, chlorobutanol, methyl paraben, propyl paraben, phenylethyl alcohol, EDTA, sorbic acid, Onamer M, or a combination thereof.

9. The thin-film forming composition of claim 5, wherein the co-solvent or surfactant comprises polysorbate 20, polysorbate 60, polysorbate 80, a polyoxyethylene surfactant, a polyoxypropylene surfactant, cyclodextrin, tyloxapol, or a combination thereof.

10. The thin-film forming composition of claim 5, wherein the viscosity builder agent comprises methyl cellulose, hydroxypropylmethylcellulose, hydroxyethylcellulose, carboxymethylcellulose, hydroxypropylcellulose, or hyaluronic acid.

11. The thin-film forming composition of claim 5, wherein the bio-adhesive agent comprises PVP, xanthan gum, locust bean gum, acacia gum, hydroxypropyl methylcellulose (HPMC), sodium alginate, pectin, gelatin, carbomer, gellan gum, tragacanth, acacia, or sodium carboxymethyl cellulose.

12. The thin-film forming composition of claim 1, wherein the composition comprises PVP-I at a concentration of 0.5% to 2.5%, the film-forming material at a concentration of 5% to 10%, ethanol at a concentration of 50% to 60% or isopropanol at a concentration of 50% to 70%, and/or ethyl acetate at a concentration of 8% to 10%.

13. The thin-film forming composition of claim 12, further comprising acetone at a concentration of 20% to 25%, castor oil at a concentration of 0.1% to 1%, or camphor at a concentration of 1% to 2%.

14. The thin-film forming composition of claim 1, further comprising sugar, potassium Iodate, potassium iodide, a local anesthetic, a topical skin adhesive, or a combination thereof.

15. The thin-film forming composition of claim 14, wherein the topical skin adhesive comprises cyanoacrylate or a derivative thereof.

* * * * *